(12) United States Patent
O'Lenick et al.

(10) Patent No.: US 7,193,111 B1
(45) Date of Patent: Mar. 20, 2007

(54) DIMER POLY-QUATERNARY COMPOUNDS

(75) Inventors: Thomas G. O'Lenick, Dacula, GA (US); Anthony J. O'Lenick, Jr., Dacula, GA (US)

(73) Assignee: Surfa Tech Corporation, Dacula, GA (US)

( * ) Notice: Subject to any disclaimer, the term of this patent is extended or adjusted under 35 U.S.C. 154(b) by 445 days.

(21) Appl. No.: 10/903,644

(22) Filed: Aug. 2, 2004

(51) Int. Cl.
*C07C 233/05* (2006.01)
*A61K 31/16* (2006.01)
*A61K 31/14* (2006.01)

(52) U.S. Cl. ............ 564/153; 564/286; 564/290; 564/295; 514/616; 514/642; 514/643

(58) Field of Classification Search ............ None
See application file for complete search history.

(56) References Cited

U.S. PATENT DOCUMENTS 5,811,385 A 9/1998 Eyrisch et al.

*Primary Examiner*—Brian Davis

(57) ABSTRACT

The present invention relates to a novel class of polymeric compounds having specific quaternized amine based upon a dimer acid reacted with an dimethyl amino propyl amine to make an amido amine, which is subsequently reacted to make a polymeric quaternary compound. Dimer acid is a C-36 diacid having a cyclic structure and two amine groups that allow for the synthesis of a high molecular weight cationic compound which is extremely substantitive to human skin and are well tolerated by human tissue making them suitable for use preparation of barrier products for personal care applications.

18 Claims, No Drawings

DIMER POLY-QUATERNARY COMPOUNDS

FIELD OF THE INVENTION

The present invention relates to a novel class of polymeric compounds having specific quaternized amine based upon a dimer acid reacted with dimethyl amino propyl amine to make an amido amine compound, which is subsequently reacted with a chlorohydroxy propyl PEG PPG product to make polymeric quaternary compounds. Dimer acid is a C-36 diacid having a cyclic structure and two amine groups that allow for the synthesis of a high molecular weight cationic compound which is extremely substantitive to human skin and are well tolerated by human tissue making them suitable for use preparation of barrier products for personal care applications.

BACKGROUND OF THE INVENTION

It is very desirable to provide a material from aqueous solution that will condition the hair and still be compatible with anionic surfactants. This allows for the preparation of clear two in one shampoo systems, clear 2 in one shower gels, and clear two in one bath products. By two in one products in meant, a product that contains both anionic surfactant, most commonly sulfates and ether sulfates and a cationic conditioning agent. The anionic surfactant is the detergent, which cleans the hair or skin, and the cationic product is for conditioning providing softness, slip and feels to the skin. The problem with such product has always been the incompatibility of the anionic and cationic surfactants with each other. When many of these products are present in the same solution an insoluble salt forms making a cosmetically unacceptable white gunk that does not stay in solution.

As will become clear, by making a very large molecule the present invention results in we call a soft quaternary compound. By soft quaternary compound is meant one that not withstanding its cationic charge is of a structure so that when placed in water along with the anionic surfactant, a clear stable solution is obtained. Surprisingly, because of the high molecular weight of the quaternary compound, the deposition on the hair and skin is increased. While not wanting to be held to only one mechanism, we believe there rather than a precipitate observed with so called hard quats, compounds of the present invention form a self-assembling complex between the anionic and cationic surfactant. This complex, while water-soluble is large enough to disrupt hydrogen bonding between water molecules, and as such energetically, the complex will be deposited on the skin or hair leaving the remaining solution at the lowest free energy level.

The self-assembling aspect of the present invention, which we believe is the result of orientation of the salt of the cationic compounds of the present invention and the anionic surfactants present in solution, can be demonstrated by the fact that upon initial mixing of the components, a hazy or cloudy dispersion occurs. With suitable mixing, this hazy dispersion becomes a solution and the viscosity increases.

The compounds of the present invention can be formulated into body washes and other skin products and hair care products to provide a "delivery system" for conditioning the hair or skin. The high molecular weight of the quat and the fact that the point charges are far apart in the molecule results in through and efficient deposition on the hair or skin. This provides uniformity of conditioning agent over the entire hair of skin surface. This is particularly important for applications on hair for people with long hair. In general the long hair is more damaged, dry and in need of conditioning at the tip area, than near the root. The hair closest to the scalp is newer, less damaged, and less in need of conditioning. This dichotomy of hair condition is more effectively treated by the complexes formed by the current invention than by other quats. In addition, the di-nature of the compounds provides for outstanding substantivity of the molecule allow for very mild natural like materials that can be used in products where low irritation is important.

U.S. Pat. No. 5,811,385 describes a process for making high active aqueous solutions of ester quats. It states "The invention relates to high-concentration aqueous solutions of quaternary carboxylic acid alkanolamine ester salts, a process for preparing these solutions and their use. Quaternary carboxylic acid alkanolamine ester salts, also named ester quats, are highly active cationic surfactants with many uses. Thus, these surfactants are suitable, for example, as fabric softeners, cosmetic bases, active compounds with respect to soil release and soil redeposition, antistatic agents, fabric finishes, biocide and phase-transfer catalysts. Since these ester quats, owing to their biodegradability, are also ecologically advantageous, they have recently substantially replaced the classic fatty alkyl quats such as distearyldimethylammonium chloride."

Ester quaternary compounds are described in U.S. Pat. No. 5,811,385. These products are not polymeric, but the patent gives a very good indication of the state of the quaternary art.

SUMMARY OF THE INVENTION

Objective of the Invention

It is the objective of the invention to provide a novel series of polymeric dimer based quaternary compounds and a process of its use which comprises contacting the skin with an effective conditioning concentration of the novel quaternary compounds when applied in aqueous solution containing anionic surfactants. These anionic surfactants are preferably fatty sulfates and fatty ether sulfates having between 1 and 4 moles of ethylene oxide present. The polymeric nature of these materials makes them very substantive and minimally penetrating to the skin, making them both non-toxic and non-irritating.

In accordance with the present invention, we have now been discovered novel quaternary compound, which conforms to the following structure:

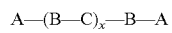

wherein:
A is

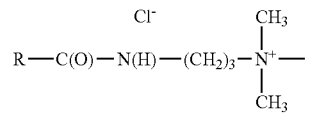

wherein;
R is alkyl having between 7 and 27 carbon atoms, and includes linear, branched, saturated, unsaturated and polyunsaturated,
B is —CH$_2$CH(OH)CH$_2$—CH$_2$CH$_2$O)$_a$—(CH$_2$CH(CH$_3$)O)(CH$_2$CH$_2$O)$_c$—CH$_2$CH(OH)CH$_2$—a, b, and c are independently integers ranging from 0 to 20, with the proviso a+b+c is at least 1;

C is selected from the group consisting of

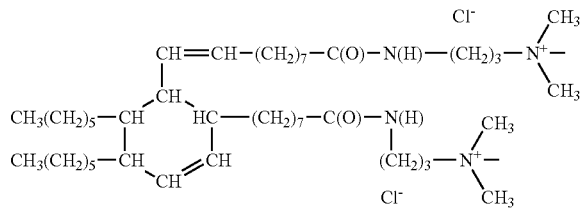

and

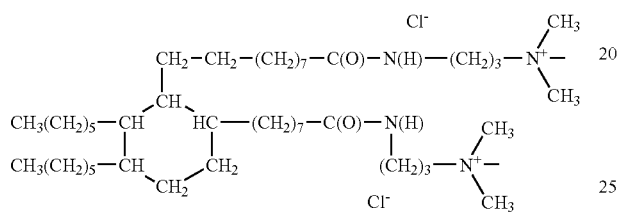

wherein;

x is an integer ranging from 1 to 2000.

The difference between the two dimer species is that one of them has no double bond in the cyclic structure, while the first has a double bond. The double bond is removed by hydrogenation of the acid prior to making the quaternary compound. This variation has lighter color and better oxidative stability, making it prized for cosmetic applications where a water white product is desired. Consumers consider water white products as cleaner and more appealing over yellow products.

The present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

The process for conditioning hair comprises contacting the hair with an effective conditioning concentration of a quaternary compound, which conforms to the following structure:

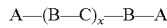

A—(B—C)$_x$—B—A wherein:

A is

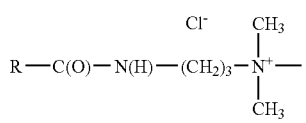

wherein;

R is alkyl having between 7 and 27 carbon atoms, and includes linear, branched, saturated, unsaturated and polyunsaturated;

B is —CH$_2$CH(OH)CH$_2$—(CH$_2$CH$_2$O)$_a$—(CH$_2$CH(CH$_3$)O)$_b$(CH$_2$CH$_2$O)$_c$—CH$_2$CH(OH)CH$_2$— a, b, and c are independently integers ranging from 0 to 20, with the proviso a+b+c is at least 1;

C is selected from the group consisting of

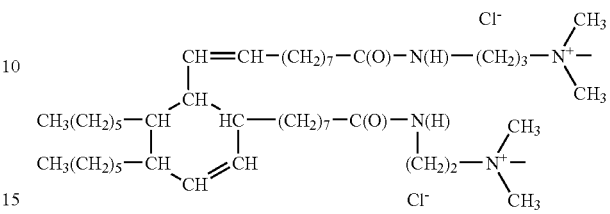

and

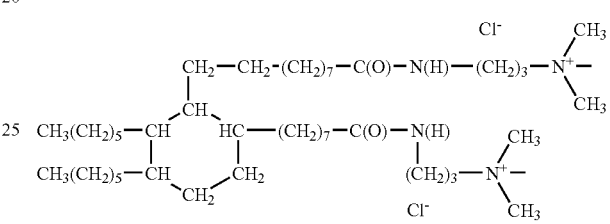

wherein;

x is an integer ranging from 1 to 2000.

The preferred effective conditioning concentration ranges from 0.5% to 25% by weight.

The polymers of the present invention are made in polar solvent, typically water, but can also be made in propylene glycol, polyoxyalkylene glycols and PEG/PPG dimethicone or combinations thereof. The selection of the proper solvent or combinations of solvents will determine the viscosity of the final polymer.

The use of PEG/PPG dimethicone as a solvent results not only in a relatively low viscosity product, but also results in a composition that has extremely efficient deposition on hair and skin, making the compositions highly desirable in personal care applications.

PREFERRED EMBODIMENTS

In a preferred embodiment R is CH$_3$(CH$_2$)$_6$—.
In a preferred embodiment, R is CH$_3$(CH$_2$)$_8$—
In a preferred embodiment, R is CH$_3$(CH$_2$)$_{10}$—
In a preferred embodiment R is CH$_3$(CH$_2$)$_{12}$—.
In a preferred embodiment, R is CH$_3$(CH$_2$)$_{14}$—
In a preferred embodiment, R is CH$_3$(CH$_2$)$_{16}$—
In a preferred embodiment R is CH$_3$(CH$_2$)$_{18}$—.
In a preferred embodiment, R is CH$_3$(CH$_2$)$_{20}$—
In a preferred embodiment, R is CH$_3$(CH$_2$)$_{22}$—
In a preferred embodiment R is CH$_3$(CH$_2$)$_{24}$—.
In a preferred embodiment, R is CH$_3$(CH$_2$)$_{26}$—
In a preferred embodiment a is 10, b is 0 and c is 0.
In a preferred embodiment a,b and c are independently integers ranging from 3 to 10
In a preferred embodiment a is 5, b is 5 and c is 5.

DETAILED DESCRIPTION OF THE INVENTION

The present invention is directed to specific quaternary compound, which conforms to the following structure:

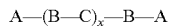

wherein:
A is

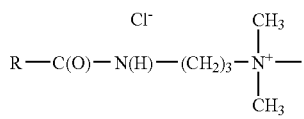

wherein;
R is alkyl having between 7 and 27 carbon atoms, and includes liner, branched, saturated, unsaturated and polyunsaturated;
B is —$CH_2CH(OH)CH_2$—$(CH_2CH_2O)_a$—$(CH_2CH(CH_3)O)_b(CH_2CH_2O)_c$—$CH_2CH(OH)CH_2$— a, b, and c are independently integers ranging from 0 to 20, with the proviso a+b+c is at least 1;
C is selected from the group consisting of

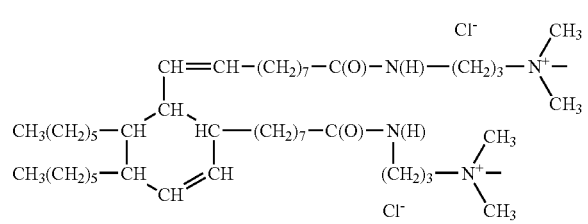

and

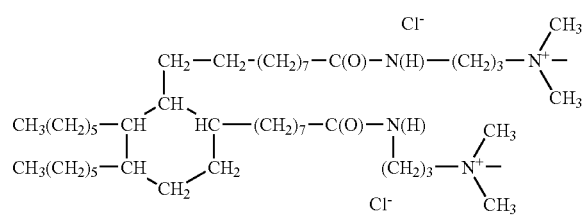

wherein;
x is an integer ranging from 1 to 2000.

The compounds of the present invention are made reaction of an alpha omega chlorohydroxy propyl PEG or PPG compound with a mixture of mono tertiary amines and di-tertiary amines in a polar solvent.

Another aspect of the present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

The process for conditioning hair comprises contacting the hair with an effective conditioning concentration of a quaternary compound, which conforms to the following structure:

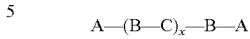

wherein:
A is

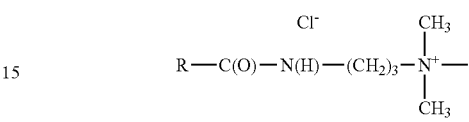

wherein;
R is alkyl having between 7 and 27 carbon atoms, and includes linear, branched, saturated, unsaturated and polyunsaturated;
B is —$CH_2CH(OH)CH_2$—$(CH_2CH_2O)_a$—$(CH_2CH(CH_3)O)_b(CH_2CH_2O)_c$—$CH_2CH(OH)CH_2$— a, b, and c are independently integers ranging from 0 to 20, with the proviso a+b+c is at least 1;
C is selected from the group consisting of

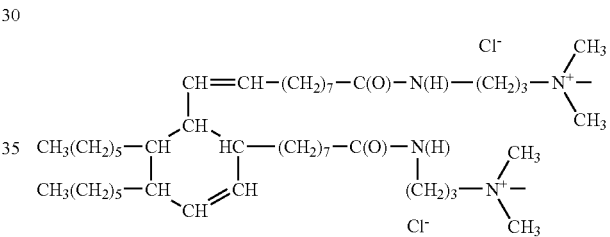

and

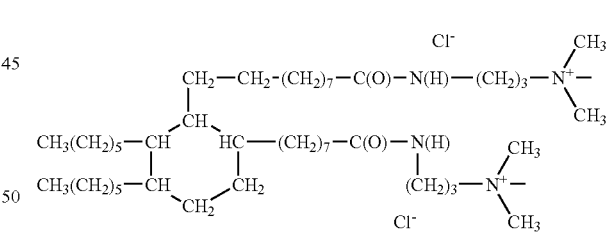

wherein,
x is an integer ranging from 1 to 2000.

The preferred effective conditioning concentration ranges from 0.5% to 25% by weight.

The inclusion of the polyoxyalkylene group into the molecules of the present invention results in improved water solubility and introduces a high cluod point nito the molecule.

The ability to modify the water solubility of the poly quaternium compounds of the present invention results in the potential to customize the substantivity of the polymer on hair, skin and fibers. This is a very important factor in developing cost effective softeners.

The compounds of the present invention are polymeric quaternary compounds and as such are well tolerated by skin and eye since their high molecular weight makes them too big to penetrate the skin.

Monofunctional Tertiary Amines

Monofunctional tertiary amines confirm to the following structure:

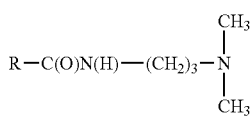

wherein;

R is alkyl having between 7 and 27 carbon atoms, and includes linear, branched, saturated, unsaturated and poly-unsaturated.

Di-functional Tertiary Amines

Di-functional tertiary amines are selected from the group consisting of compounds conforming to the following structures:

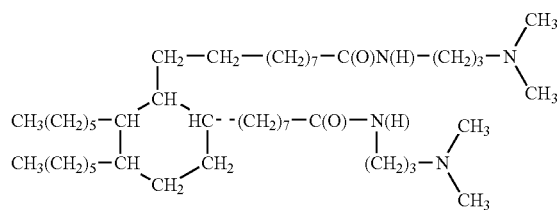

and

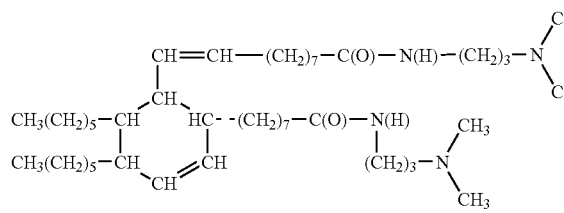

The polymerization process continues with the monofunctional tertiary amine being the chain terminator (A) unit, the hydroxy-propyl group being the (B) unit and the dysfunctional tertiary amine being the (c) unit. The product of the present invention is thereby attained as a polyquaternium. The higher the concentration of monofunctional tertiary amine, the lower the value of "x". If no di-tertiary amine is added, x is 0, resulting in a bis-quat not a polymer. The polymer is not made with vinyl monomer, thereby making it vinyl monomer free and avoiding the toxicological problems inherent to levels of unreacted monomer left in vinyl polymers.

The compatibility of this novel quaternary compounds of the invention with human tissue, i.e., dermal and eye tissue has been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

EXAMPLES

Dimer Acid and Hydrogenated Dimer Acid

Dimer acid and hydrogenated dimer acids are items of commerce commercially available from several suppliers, one of which is Cognis Corporation, formerly the Emery Division of Henkel.

Dimer acid conforms to the following structure;

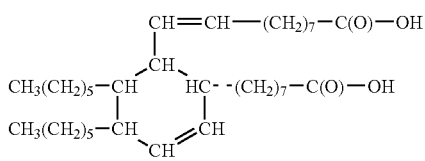

Hydrogenated dimer acid conforms to the following structure;

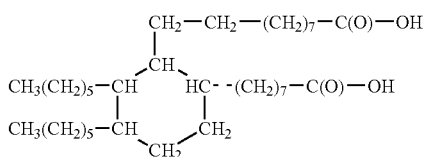

DMAPA

Dimethylaminopropyl Amine (DMAPA) is an item of commerce available from a variety of sources including Dow Chemical.

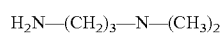

Alpha Omega Di-chloro-2-hydydroxy propyl PEG/PPG

Compounds of this class are available from Siltech LLC, Dacula, Ga. They conform to the following structure:

$C_1$—$CH_2CH(OH)CH_2$—$(CH_2CH_2O)_a$—$(CH_2CH(CH_3)O)_b$ $(CH_2CH_2O)_c$—$CH_2CH(OH)CH_2$—Cl a, b, and c are independently integers ranging from 0 to 20, with the proviso a+b+c is at least 1;

| Example | a | b | c |
|---------|-----|-----|-----|
| 1 | 9 | 0 | 0 |
| 2 | 20 | 20 | 20 |
| 3 | 5 | 5 | 5 |
| 4 | 10 | 1 | 10 |
| 5 | 5 | 1 | 5 |
| 6 | 20 | 0 | 0 |
| 7 | 10 | 5 | 0 |
| 8 | 2 | 5 | 5 |
| 9 | 1 | 0 | 0 |
| 10 | 0 | 1 | 0 |

Mono-Functional Tertiary Amines

Monofunctional Tertiary amines conform to the following structure:

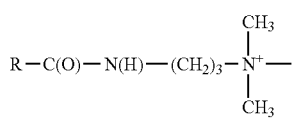

wherein;

R is alkyl having between 7 and 27 carbon atoms, and includes linear, branched, saturated, unsaturated and poly-unsaturated.

Preparation of the Mono Functional Tertiary Amines

The mono functional tertiary amines (Examples 1–8) are prepared according to the following procedure:

To 400.0 grams of the specified acid is added 200.0 grams of dimethyl amino propyl amine. The mixture is heated to 180–200° C., keeping the temperature of the distillate coming off at no more than 102° C. This temperature assures that minimal amounts of the amine distill off with the water made during the reaction. Once the temperature reaches 200° C. hold for 3–8 hours. An excess of the amine is added to speed up the reaction. When the acid value reaches 1.0 mg KOH/gram, the excess amine is stripped off by applying vacuum. The resulting product is the amido amine is useful as an intermediate in the preparation of the compounds of the present invention.

| Example | Acid |
|---------|------|
| 11 | Caprylic Acid |
| 12 | Capric Acid |
| 13 | Lauric Acid |
| 14 | Myristic Acid |
| 15 | Palmitic Acid |
| 16 | Stearic Acid |
| 17 | Oleic Acid |
| 18 | Behenic Acid |

Di-functional Tertiary Amines

Example 19

Preparation of Dimer Amido Amine

To 561.0 grams of dimer acid is added 200.0 grams of dimethyl amino propyl amine. The mixture is heated to 180–200° C., keeping the temperature of the distillate coming off at no more than 102° C. This temperature assures that minimal amounts of the amine distill off with the water made during the reaction. Once the temperature reaches 200° C. hold for 3–8 hours. An excess of the amine is added to speed up the reaction. When the acid value reaches 1.0 mg KOH/gram, the excess amine is stripped off by applying vacuum. The resulting product is the dimer amido amine is useful as an intermediate in the preparation of the compounds of the present invention. The product is a yellow water insoluble liquid at ambient temperatures.

Example 20

Preparation of Dimer Amido Amine

To 561.0 grams if dimer acid is added 200.0 grams of dimethyl amino propyl amine. The mixture is heated to 180–200° C., keeping the temperature of the distillate coming off at no more than 102° C. This temperature assures that minimal amounts of the amine distill off with the water made during the reaction. Once the temperature reaches 200° C. hold for 3–8 hours. An excess of the amine is added to speed up the reaction. When the acid value reaches 1.0 mg KOH/gram, the excess amine is stripped off by applying vacuum. The resulting product is the dimer amido amine which is useful as an intermediate in the preparation of the compounds of the present invention. The product is a yellow water insoluble liquid at ambient temperatures.

Example 21–29

Preparation of the Cationic of the Present Invention

Into a suitable reaction flask is charged the specified number of grams of the specified solvent. Next, add the specified number of grams of the alpha omega dichloro 2 hydroxy propyl PEG PPG (Example 1–10). Heat is applied to 90° C. Next, the specified number of grams of the specified dimer amido amine (either example 19 or 20), followed by the specified number of grams of the specified mono tertiary amine (examples 11–18) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

Example 21–29

| | Solvent | | Mono Amine | | Di Amine | | Dichloro-PEG/PPG | |
|---------|------|-------|---------|-------|---------|-------|---------|-------|
| Example | Type | Grams | Example | Grams | Example | Grams | Example | Grams |
| 21 | Water | 185.7 | 1 | 9.6 | 8 | 75.5 | 1 | 5.9 |
| 22 | Water | 150.0 | 2 | 5.6 | 9 | 78.8 | 2 | 31.4 |
| 23 | DMC | 50.0 | 3 | 2.6 | 8 | 81.4 | 3 | 9.1 |
| | Water | 50.0 | | | | | | |
| 24 | PG | 300.0 | 4 | 1.4 | 9 | 82.3 | 4 | 11.4 |
| 25 | Water | 81.8 | 5 | 2.3 | 8 | 81.6 | 5 | 7.0 |
| 26 | Water | 100.0 | 6 | 25.5 | 8 | 62.3 | 6 | 10.8 |
| 27 | PEG | 185.7 | 7 | 6.8 | 8 | 77.8 | 7 | 9.3 |
| 28 | Water | 185.7 | 8 | 0.4 | 8 | 83.2 | 8 | 8.0 |

-continued

| | Solvent | | Mono Amine | | Di Amine | | Dichloro-PEG/PPG | |
|---|---|---|---|---|---|---|---|---|
| Example | Type | Grams | Example | Grams | Example | Grams | Example | Grams |
| 29 | Water | 150.0 | 9 | 17.3 | 8 | 69.0 | 9 | 2.4 |
| 30 | Water | 150.0 | 9 | 17.3 | 8 | 69.0 | 10 | 2.6 |

DMC is PEG10 Dimethicone a commercial product marketed by Siltech LLC Dacula, Ga. as SILSURF Di1010.

PEG is polyoxyethylene glycol having a molecular weight of 400, marketed commercially by Phoenix Chemical Inc. Somerville, N.J.

PG is propylene glycol, marketed commercially by Phoenix Chemical Inc Somerville, N.J.

Additional Information

| Example | x value | % Solids |
|---|---|---|
| 21 | 10 | 35 |
| 22 | 20 | 40 |
| 23 | 50 | 50 |
| 24 | 10 | 25 |
| 25 | 1 | 55 |
| 26 | 67 | 50 |
| 27 | 5 | 35 |
| 28 | 600 | 35 |
| 29 | 10 | 40 |

The products of the present invention range from low viscosity (300 cps for example 15) to a solid gel for example 19. The key to viscosity is the degree of polymerization (d.p.) which is reflected in the "x" value. As the "x" value increases the molecular weight of the resultant polymer increases and the % by weight of the mono tertiary amine decreases. Viscosity can also be lowered by using a non-aqueous polar solvent like propylene glycol or butylene glycol.

APPLICATIONS EXAMPLES

The higher the molecular weight, the less likely the compound is to penetrate the skin. Since contact with skin is expected in washing the hair, even for hair use the higher molecular weight components are desired. The polymers of the present invention are not made by free radical polymerization. Consequently, they have no residual monomer content. This has become a major issue in selecting polymers for personal care.

The compounds of the present invention provide outstanding wet comb and conditioning properties to hair. They reduce static build up and provide gloss. The polymers of the present invention provide an outstanding smooth dry feel on the skin. The polymers of the present invention are non-toxic, and non-irritating.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A quaternary compound which conforms to the following structure:

$$A-(B-C)_x-B-A$$

wherein:

A is

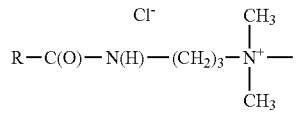

wherein;

R is alkyl having between 7 and 27 carbon atoms, and includes linear, branched, saturated, unsaturated and polyunsaturated;

B is —$CH_2CH(OH)CH_2$—$(CH_2CH_2O)_a$—$(CH_2CH(CH_3)O)_b(CH_2CH_2O)_c$—$CH_2CH(OH)CH_2$— a, b, and c are independently integers ranging from 0 to 20, with the proviso a+b+c is at least 1;

C is selected from the group consisting of

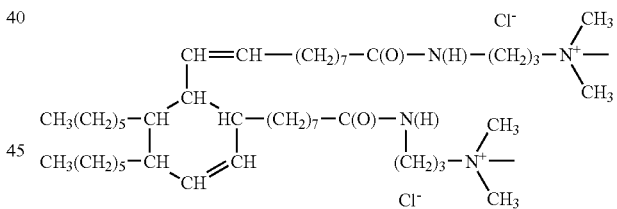

and

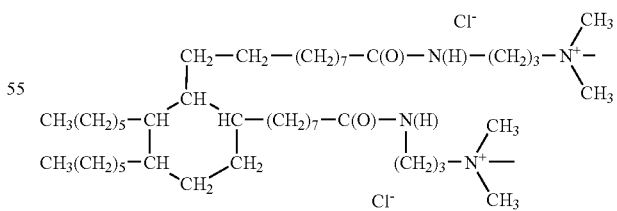

wherein;

x is an integer ranging from 1 to 2000.

2. A quaternary compound of claim 1 wherein R is $CH_3(CH_2)_6$—.

3. A quaternary compound of claim 1 wherein R is $CH_3(CH_2)_8$—.

4. A quaternary compound of claim 1 wherein R is $CH_3(CH_2)_{10}-$.

5. A quaternary compound of claim 1 wherein R is $CH_3(CH_2)_{12}-$.

6. A quaternary compound of claim 1 wherein R is $CH_3(CH_2)_{14}-$.

7. A quaternary compound of claim 1 wherein R is $CH_3(CH_2)_{16}-$.

8. A quaternary compound of claim 1 wherein R is $CH_3(CH_2)_{18}-$.

9. A quaternary compound of claim 1 wherein R is $-CH_3(CH_2)_{22}-$.

10. A process for conditioning the skin and hair which comprises contacting the hair with an effective conditioning concentration of a quaternary compound, which conforms to the following structure:

$$A-(B-C)_x-B-A$$

wherein:

A is

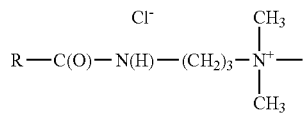

wherein;

R is alkyl having between 7 and 27 carbon atoms, and includes linear, branched, saturated, unsaturated and polyunsaturated;

B is $-CH_2CH(OH)CH_2-(CH_2CH_2O)_a-(CH_2CH(CH_3)O)_b(CH_2CH_2O)_cCH_2CH(OH)CH_2-$ a, b, and c are independently integers ranging from 0 to 20, with the proviso a+b+c is at least 1;

C is selected from the group consisting of:

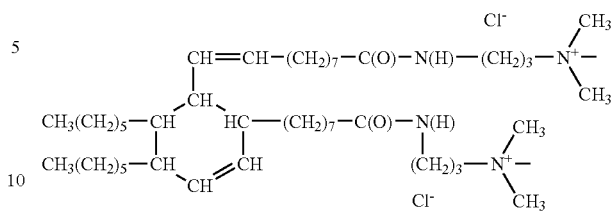

and

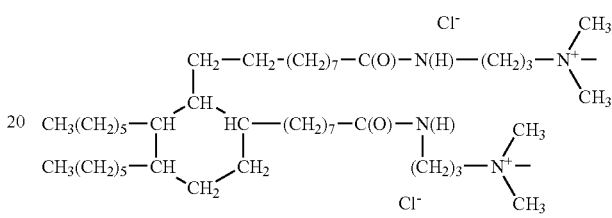

wherein;

x is an integer ranging from 1 to 2000.

11. A process of claim 10 wherein R is $CH_3(CH_2)_6-$.

12. A process of claim 10 wherein R is $CH_3(CH_2)_8-$.

13. A process of claim 10 wherein R is $CH_3(CH_2)_{10}-$.

14. A process of claim 10 wherein R is $CH_3(CH_2)_{12}-$.

15. A process of claim 10 wherein R is $CH_3(CH_2)_{14}-$.

16. A process of claim 10 wherein R is $CH_3(CH_2)_{16}-$.

17. A process of claim 10 wherein R is $CH_3(CH_2)_{18}-$.

18. A process of claim 10 wherein R is $-CH_3(CH_2)_{22}-$.

* * * * *